United States Patent [19]
Murakami et al.

[11] Patent Number: 5,792,869
[45] Date of Patent: Aug. 11, 1998

[54] PROCESS FOR PREPARING OPTICALLY ACTIVE PIPERAZINE DERIVATIVES AND INTERMEDIATES FOR PREPARATION

[75] Inventors: Hisamichi Murakami; Shoko Satoh; Tadashi Tobiyama; Ken'ichi Sakai, all of Tokyo; Hiroyuki Nohira, Urawa, all of Japan

[73] Assignee: Yamakawa Chemical Industry Co., Ltd., Tokyo, Japan

[21] Appl. No.: 552,089

[22] Filed: Nov. 2, 1995

[30] Foreign Application Priority Data

| Nov. 4, 1994 | [JP] | Japan | 6-271565 |
| Apr. 11, 1995 | [JP] | Japan | 7-085814 |
| Aug. 4, 1995 | [JP] | Japan | 7-200098 |

[51] Int. Cl.$^6$ .................................... C07D 241/04
[52] U.S. Cl. ........................... 544/390; 544/360
[58] Field of Search .................................... 544/390

[56] References Cited

U.S. PATENT DOCUMENTS

| 5,413,999 | 5/1995 | Vacca et al. | 514/231.5 |
| 5,463,067 | 10/1995 | Askin et al. | 548/113 |

FOREIGN PATENT DOCUMENTS

| 604185 | 6/1994 | European Pat. Off. |
| 4-18084 | 1/1992 | Japan |
| 4-169558 | 6/1992 | Japan |
| 5-279325 | 10/1993 | Japan |
| 5-279326 | 10/1993 | Japan |
| 7-188124 | 7/1995 | Japan |
| WO 94/18192 | 8/1994 | WIPO |
| WO 94/26717 | 11/1994 | WIPO |
| WO 95/02583 | 1/1995 | WIPO |
| WO 95/02584 | 1/1995 | WIPO |
| WO 95/21162 | 1/1995 | WIPO |

OTHER PUBLICATIONS

Nakai et al., Chemical Abstracts, vol. 116, No. 255640 (1992).
Nakai et al, Chem. Abstracts, vol. 124, No. 86055 (Abstract for JP 07,188124, Jul. 25, 1995), (1996).
Ito et al, Chemical Abstracts vol. 120, Nos. 217267 and 217268 (Abstract for JP05279325 & JP05279326, Oct. 26, 1993) (1994).
Nakai et al, Chemical Abstracts, vol. 117, No. 212000 (Abstract for JP 04,169558, Jun. 17, 1992) (1992).
Watanabe et al, Chem Abstracts vol. 124, No. 176150 (1996).
Oyamada et al. Chem. Abstracts vol. 125, No. 32904 (1996).
Felder et al, Helvetica Chimica Acta, 43 888–896 (1960).
Askin et al, Tetrahedron Letters, vol. 35, No. 5, pp. 673–676 (1994).
Vacca et al, Proc. Natl. Acad. Sci. USA, 91, pp. 4096–4100 (Apr. 1994).
S. Stinson, Chem. & Eng. pp. 6–7, (May 16, 1994).
Bigge et al, Tetrahedron Lett., 30, pp. 5193–5196 (1989).
Dorsey et al, Med. Chem. 37, No. 21, pp. 3443–3451 (1994).

Primary Examiner—Emily Bernhardt
Attorney, Agent, or Firm—Armstrong, Westerman, Hattori, McLeland & Naughton

[57] ABSTRACT

Process for preparing optically active 2-piperazine-carboxylic acid derivatives, particularly S-enantiomer thereof, in high yield and high optical purity on industrial scale. As the optical resolving agents, easily accessible sulfonamides derived from selected optically active amino acids, such as N-tosyl-L-phenylalanine, N-tosyl-D-phenylglycine, N-tosyl-L-alanine or N-tosyl-L-valine, give excellent results. These resolving agents are stable and easily recovered from the reaction mixture and reused. Resolved 2-piperazinecarboxylic acid derivatives are preferably isolated as 4-t-butoxycarbonyl (Boc) derivatives. Diastereomeric salts (an example being shown below) formed as the intermediates of resolution are novel.

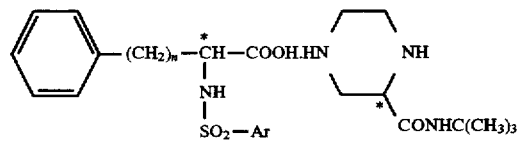

[In the formula "Ar" stands for a phenyl or naphthyl group which may be substituted with one to three C1–C6 alkyl groups, halogen atoms, nitro or alkoxy groups; and n=0 or 1.]

11 Claims, 3 Drawing Sheets

PROCESS FOR PREPARING OPTICALLY ACTIVE PIPERAZINE DERIVATIVES AND INTERMEDIATES FOR PREPARATION

BACKGROUND OF THE INVENTION

The present invention concerns optically active piperazine derivatives, particularly, N-t-butyl-2-piperazinecarboxamide. The invention also concerns diastereomeric salts, which are novel chemical compounds obtained as the intermediates in the process of preparing the optically active compounds.

Recent violent spread of AIDS worldwide promoted major pharmaceutical companies to develop various remedies to control the disease and several HIV protease inhibitors, which inhibit an enzyme essential to the virus's life cycle, are under development as one of the most promising drugs to AIDS. Merck & Co. of Rahway, N.J., has selected a protease inhibitor designated as L-735,524 from numerous candidates as the most potent and efficacious compound. Its chemical structure is disclosed to be the formula VIII

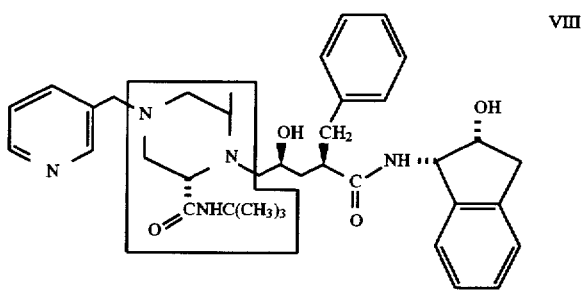

[J. P. Vacca et al., European patent 541,168, also U.S. Pat. No. 5,413,999; D. Askin et al., Tetrahedron Lett., 35(5), 673–6 (1994); J. P. Vacca et al., Proc. Natl. Acad. Sci. USA, 91, 4096–4100 (1994); also cf. Chem. & Eng. News, May 16, 1994, p6].

There has been devised and developed several synthesis routes for VIII, but all the process utilize (S)-N-t-butyl-2-piperazinecarboxamide I or its Boc-protected derivative IX as one of the key intermediates.

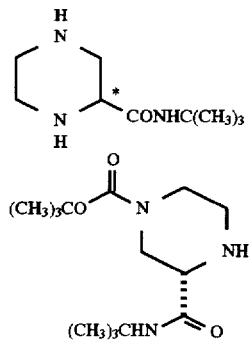

D. Askin et al [loc.cit.; also WO 95/02583 and WO 95/02584 (both Jan. 26, 1995)] describe an outline of the synthesis of (S)-IX starting from pyrazinecarboxylic acid, condensing it with t-butylamine to an amide derivative, hydrogenating the pyrazine ring to piperazine, then the obtained racemic carboxamide is combined with two equivalents of (S)-camphorsulfonic acid to give a sulfonate salt of (S)-I. This is a modification of the process of Felder et al. [Helv. Chim. Acta, 43 888–896] who have accomplished the resolution of 2-piperazinecarboxylic acid by using two equivalents of (S)-camphorsulfonic acid to obtain (S)-carboxylic acid salt with two molecules of (S)-sulfonic acid. Askin et al. transformed the above mentioned sulfonate salt of (S)-I directly to its t-butoxycarbonyl-protected derivative IX by reacting the salt with di-t-butyl dicarbonate in the presence of triethylamine.

It is also disclosed that racemate of I is resolved by using (S)-pyroglutamic acid, which is prepared by ring closure of commercially available L-glutamic acid, as a resolving agent. As (S)-pyroglutamic acid forms the less soluble diastereomeric salt with (R)-N-t-butyl-2-piperazinecarboxamide, the wanted (S)-carboxamide should be isolated from the mother liquor of the resolution in a laborious process which does not always give highly optically pure product.

Another drawback of these known resolving agents is their extremely high solubility in water, which results in the difficulty of the recovery of used resolving agents from the reaction mixtures. A large quantity of expensive resolving acids should be thrown into a waste water treatment system and degraded by microbes.

In order to produce (S)-N-t-butyl-2-piperazinecarboxamide, a key component to L-735,524, at a reasonable cost and in an environmentally friendly way, it is essential to find an efficient and easily recoverable resolving agent and carry out the resolution smoothly and economically.

SUMMARY OF THE INVENTION

An object of the present invention is to improve the technology for optical resolution of the piperazine derivatives expressed by formula I, more specifically, to provide an improved process for preparing optically active N-t-butyl-2-piperazinecarboxamide.

The diastereomeric salts formed in the process of the present optical resolution are novel compounds, and it is also an object of the invention to provide these compounds.

DETAILED EXPLANATION OF THE PREFERRED EMBODIMENTS

Figure 1:
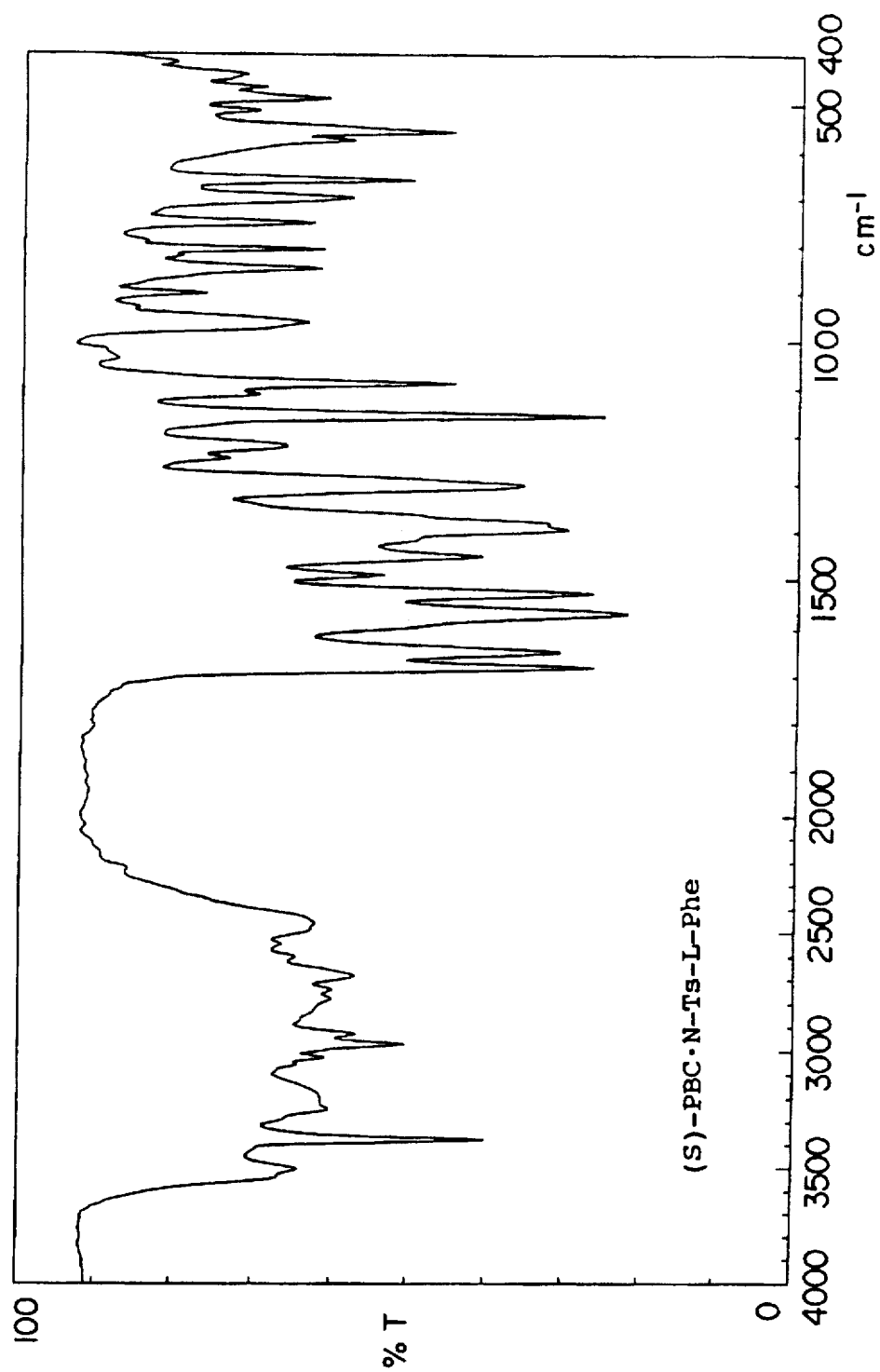
FIG. 1 is a chart of IR absorption spectrum of purified salt of (S)-N-t-butyl-2-piperazinecarboxamide N-tosyl-L-phenyl-alanine, which is a diastereomeric salt obtained in working example 1.

The process of preparing optically active piperazine derivatives of the present invention comprises the steps of:

(1) combining (RS)-N-t-butyl-2-piperazinecarboxamide expressed by formula I, which is hereinafter referred to as "PBC":

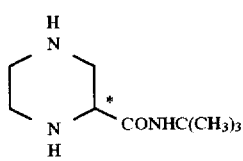

with an optical resolving agent which is a sulfonamide derivative of optically active amino acids expressed by general formulas II to IV:

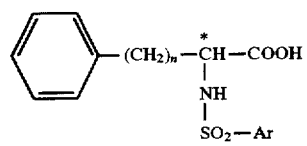

[in formula II Ar stands for a phenyl or naphthyl group which may be substituted with one to three $C_1$–$C_6$ alkyl groups, halogen atoms, nitro or alkoxy groups; and n=0 or 1.]

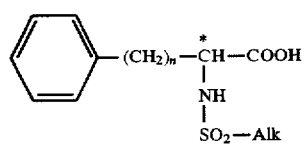

[in formula III Alk stands for a $C_1$–$C_6$ alkyl group; and n=0 or 1.]

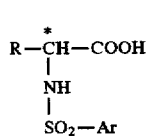

[in formula IV R stands for a straight-chain or branched-chain $C_1$–$C_6$ alkyl group, methylthioethyl group or a $C_1$–$C_2$ hydroxyalkyl group; Ar stands for phenyl or naphthyl group which may be substituted with one to three $C_1$–$C_6$ alkyl groups, halogen atoms, nitro or alkoxy groups.] in a reaction medium to form diastereomeric salts of general formulas V to VII:

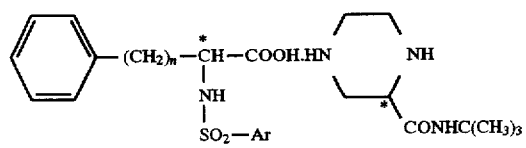

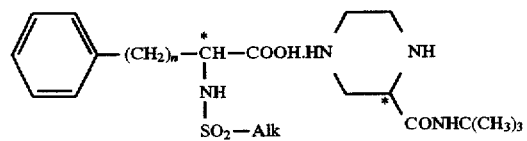

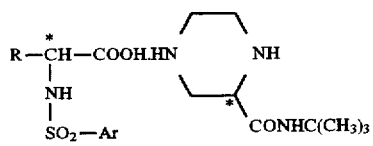

[in formula VII R and Ar have the meanings defined above]

(2) precipitating the less soluble diastereomeric salt out of the formed diastereomeric salts in the medium, and separating the precipitated less soluble diastereomeric salt from the medium; and (3) decomposing the salt to obtain optically active N-t-butyl-2-piperazinecarboxamide.

Among the optical resolving agents expressed by general formulas II to IV above, particularly important ones are: those classified in the group of general formula II, such as N-tosyl-L-phenylalanine, formula IIa, (hereinafter abbreviated as "N-Ts-L-Phe") and N-tosyl-D-phenylglycine, formula IIb, (hereinafter abbreviated as "N-Ts-D-PG"); and those classified in the group of general formula IV, such as N-tosyl-L-alanine, formula IVa, (hereinafter abbreviated as "N-Ts-L-Ala"), N-tosyl-D-alanine, and N-tosyl-L-valine, formula IVb, (hereinafter abbreviated as "N-Ts-L-Val"):

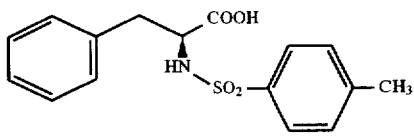

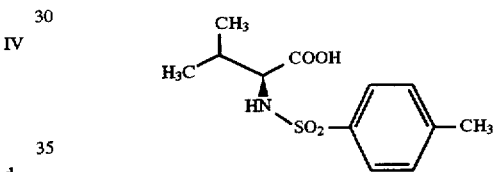

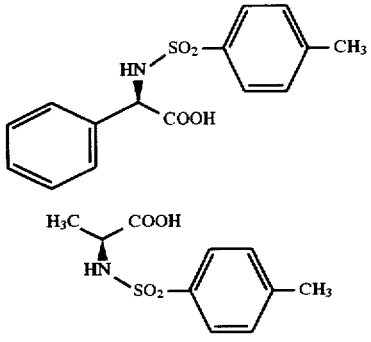

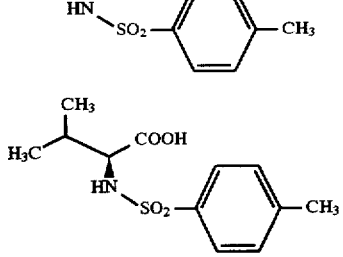

Of the optical resolving agents used in the present invention some are known and the others, majority of them, are novel compounds. These compounds may be synthesized by, a conventional method, reacting corresponding amino acids with appropriate sulfonic acid halides or anhydrides. As the sulfonic acid halide the chloride is easily available and generally gives amides at high yields. Synthesis may be carried out by so-called "Schotten-Baumann Process" which comprises dissolving an amino acid as an alkali metal salt in a reaction medium and adding an acid chloride under neutralization of hydrogen chloride which is liberated during the reaction.

The compounds of general formulas II to IV generally crystallize readily, and solubilities thereof in water are relatively low. Therefore, they can be easily recovered as the free acids at high yields by acidifying the alkaline solution with a mineral acid.

The optical resolving agents II to IV synthesized by the above described method may have, as they are, sufficient chemical purities and optical purities for reuse in the resolution. However, when necessary, it is possible to purify them by recrystallizing from a suitable solvent such as a lower alcohol, a water-containing lower alcohol, or aromatic hydrocarbons such as benzene and toluene, or a mixed solvent of an aromatic hydrocarbon and an aliphatic hydrocarbon such as hexane. Alternatively, acidification of an alkaline solution of crude carboxylic acids with a mineral acid such as hydrochloric or sulfuric acid to precipitate the carboxylic acid may be effective to improve purities.

To prepare diastereomeric salts V to VII from amide I and resolving agents II to IV, the following procedures are employed: compound I and one of compounds II to IV are mixed with a solvent and the mixture is heated to a temperature up to the boiling point of the solvent to dissolve, and then, the solution is cooled to crystallize out less soluble diastereomeric salts V to VII. It is preferable to add a small quantity of the desired salt as seed crystals to facilitate the crystallization of a salt with higher optical purity. In the process of the present invention, salts of good to very high optical purities are usually obtained, however, it is essential to use proper amount of solvent and cool the solution gradually so as to avoid rapid crystallizing out and to form well grown crystals of the salt. Solid-liquid separation may be carried out using a conventional filtering device or centrifuge. Rinsing with a suitable solvent gives diastereomeric salts with sufficient purities. Purification of the obtained diastereomeric salt will be carried out by further recrystallization from a suitable solvent. In general, single recrystallization is sufficient to prepare practically acceptable high optical purity.

As the reaction medium there may be used various solvents such as water, methanol, ethanol, n-propanol, isopropanol, n-butanol, isobutanol, pentanol, hexanol, benzene, toluene, ethyl acetate, methyl ethyl ketone, methyl isobutyl ketone, dioxane, dimethyl formamide, dimethyl sulfoxide, diethyl ether, diisopropyl ether, and mixtures thereof. Particularly, lower alcohols such as methanol and ethanol, and a mixed solvent of alcohols are suitable.

Addition of water to the lower alcohol causes significant changes in solubilities of the diastereomers, and thus, use of the mixed solvent containing a suitable proportion of water makes it possible to improve the optical purity of the salt formed or to decrease necessary amount of the solvent. In case of methanol, addition of 10–30% water decreases the necessary amount of the solvent to one half of the pure solvent, and therefore, brings about remarkable improvement in the productivity.

Furthermore, in the case where an alanine derivative is used as the resolving agent, as shown in the working examples described later, steric configuration of PBC obtained may be reversed depending on the solvent, i.e., from alcoholic solution a salt of PBC with R-configuration is obtained, while a salt of (S)-PBC is obtained from aqueous solution. Suitable selection and combination of the resolving agents and the solvents will thus give desired enantiomer of PBC.

The resolving agents are used in an amount ranging from 0.1 to 2.0 in molar ratio to PBC to be resolved. Preferable range is 0.5 to 1.0. Although PBC is a diacidic base and sulfonamide derivatives of amino acids used as the resolving agents are monobasic acids, 1:1-salts precipitate as the less soluble diastereomeric salts, and therefore, it is of little use to choose a molar ratio exceeding 1.0. As the molar ratio decreases from 1.0 the yield of the diastereomeric salts decreases. Practically sufficient amount of the salt will precipitate even at a molar ratio of 0.5.

In the optical resolution of piperazine-2-carboxylic acid with camphorsulfonic acid there is formed a diastereomeric salt in which two molecules of the resolving agent are combined with the piperazine compound. In the present process, one molecule of PBC, which is a diacidic base, and one molecule of the sulfonamide derivative of optically active amino acids, which is a monoacidic base, form a diastereomer for achieving the resolution. This is a surprising and unexpected discovery, and the fact that efficient optical resolution can be accomplished using a smaller amount of resolving agent is very important factor for industrial practice.

The novel compounds provided by the present invention are diastereomers expressed by the general formulas V and VII below. It happens sometimes that molecules of water or a solvent are included in the crystal of the salts to make the crystal structure stable.

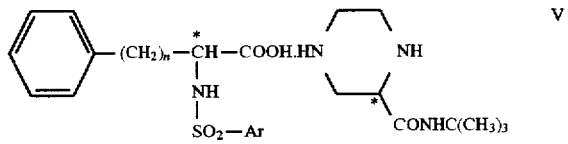

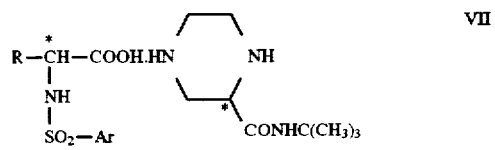

After selective crystallization of the less soluble diastereomeric salt in the above described process, the antipode of PBC remains dissolved in the mother liquor as the more soluble salt. The remaining PBC may be recovered from the solution and recemized by heating with a base to provide a material for further resolution. The racemization proceeds without difficulty, and can be practiced in accordance with the known technology.

The less soluble diastereomeric salt obtained by the selective crystallization may be readily decomposed by reacting with an acid or a base to recover the optically active PBC. Usually, this is practiced by adding an acid to the diastereomeric salt to precipitate the resolving agent and filtering the precipitate, or by extracting the resolving agent with a suitable organic solvent and separating from acidic solution of PBC. The target optically active PBC is used as its Boc-protected derivative in the synthetic procedure of HIV protease inhibitor, it is advisable to react a protecting agent with the diastereomeric salt to derive PBC to 4-t-butoxycarbonyl derivative, then to separate it from the resolving agent.

Among the available Boc-protecting agents, for example, t-butoxycarbonyl chloride (Boc-Cl), t-butyl azidoformate (Boc-N₃), 2-(t-butoxycarbonyloxyimino)-2-phenyl acetonitrile (Boc-ON), or 2-(t-butoxycarbonylthio)-4,6-dimethyl pyrimidine (Boc-S), di-t-butyl dicarbonate (Boc₂O) is easy to handle and does not form unfavorable by-products. More specifically, di-t-butyl dicarbonate is reacted to the diastereomeric salt in the presence of triethylamine, and the resulting N-t-butyl-4-t-butoxycarbonyl-2-piperazinecarboxamide (Boc-PBC) is extracted with a solvent to separate from the salt of the resolving agent. 4-t-Butoxycarbonyl group is readily eliminated by an acid treatment of Boc-PBC to give optically active N-t-butyl-2-piperazinecarboxamide.

The optical resolving agents are recovered at a high yield by acidifying the aqueous solution of the alkali metal salts or amine salts thereof with a strong acid, and separating the precipitates by filtration.

Introduction of various substituents into the Ar-group of resolving agents II and IV results in the significant change of yields and optical purities of the obtained salts. For example, introduction of an alkyl group or a halogen atom at p- or o-position of the phenyl ring increases yields and optical purities of the diastereomeric salts. Particularly, a compound II having an o- or p-methyl-, p-t-butyl-, p-chloro- or p-bromo-substituted phenyl gives a salt of optical purity of 97% or higher at a yield of 95% or more. Increase in number of methyl substituents is rather detrimental. Particularly, with the 2,4,6-tri-substituted compound precipitation of the salt tends to be slow and the yield decreases heavily. A compound II which is derived from L-phenylalanine and having a sterically crowded 2,4,6-triisopropylphenyl group forms a less soluble salt with (R)-I contrary to the other L-phenylalanine derivatives.

When Ar of compound II is 1- or 2-naphthyl instead of phenyl group moderate resolutions are resulted. Compounds substituted with strongly polar groups such as methoxy and nitro, give a somewhat inferior performance as resolving agents compared to the alkyl-substituted agents.

As to the optical resolving agents II and IV, compounds having a monomethyl-substituted Ar-group, particularly, easily available p-methyl-substituted compounds give the best results in regard to yield and optical purity of the products.

Aromatic amino acids which are starting materials for resolving agents II and III are, phenylglycine, in the case of n=0, and phenylalanine, in the case of n=1. D- or (R)-phenyl-glycine is commercially manufactured as an intermediate of ampicillin, an antibiotic, and L- or (S)-phenylalanine as a raw material of aspartame, one of the most widely used sweetening agents, and these amino acids are easily available at a reasonable price. Resolving agents II of S-configuration synthesized from L-phenylalanine generally forms less soluble salts with S-enantiomer of piperazine derivative I, while compound II of R-configuration derived from D-phenylglycine forms less soluble salts with R-enantiomer of I. Thus, it is possible to obtain both R- and S-enantiomer of piperazine derivatives.

The amino acids used as the starting material for resolving agents IV are L- or D-amino acids having a straight or branched chain alkyl group such as alanine, alpha-aminobutyric acid, valine, leucine and isoleucine, or those with substituted alkyl group such as methionine, seline and threonine. Especially suitable materials are easily available D- and L-alaine, valine, L-leucine and L-isoleucine. On one hand, p-toluenesulfonamide IV (Ar=p-tolyl) derived from L-amino acid such as L-valine and L-leucine forms less soluble salts with (S)-I. On the other hand, compound IVa (R=methyl), which is a derivative of L-alanine forms the less soluble salt with (R)-I. Thus, selective production of both R- and S-enantiomer of compound I is possible using easily available L-amino acid. By using a p-toluenesulfonamide IV (R=methyl) derived from D-alanine, the less soluble salt with (S)-I precipitates, while (R)-I forms a less soluble salts with resolving agent IV derived from D-valine (R=isopropyl).

The present invention enables an improved production of optically active piperazine derivatives, particularly, N-t-butyl-2-piperazinecarboxamide, with high yield and excellent optical purity. Sulfonamide derivatives of optically active amino acids are used as resolving agents in an equimolar amount or less to the racemic piperazine derivatives to be resolved, and can be easily recovered and reused in the next resolution batches. The unwanted enantiomer of the piperazine derivatives can be recovered from the mother liquor of resolution and easily racemized to provide the starting material.

Further advantages of the present invention reside in the high optical purities of the precipitated less soluble diastereomeric salts and their easiness of purification to optically pure ones, less expensive solvents, such as methanol, ethanol or even water are utilized in the resolution.

All these improvements contribute to significantly lower the production cost of the optically active piperazine derivatives, comparing to the known processes.

EXAMPLES

Preparation of Resolving Agent 1
N-Tosyl-L-phenylalanine (N-Ts-L-Phe)

A dispersion of L-phenylalanine 4.95 g (30mmol) in a mixture of water 15 ml and 2 N sodium hydroxide 36 ml was cooled in an ice-water bath, and under vigorous stirring a mixture of p-toluenesulfonyl chloride 6.86 g (36 mmol) and tetrahydrofuran 12 ml was added dropwise thereto.

After completion of the addition, stirring was continued under ice-water cooling for 10 minutes, and further at room temperature for 1 hour. Then, 2 N hydrochloric acid 21.5 ml was added, and resulting N-Ts-L-Phe was extracted with chloroform 100 ml. Organic layer was rinsed with water and dried. By distilling off the solvent 8.32 g of crude N-Ts-L-Phe was obtained. The yield based on the used L-phenylalanine was 86.9%. The crude N-Ts-L-Phe was recrystallized once from isopropanol-water mixture to give 5.78 g of fine crystalline N-Ts-L-Phe. The overall yield was 60.4%. Melting point: 160.0°–161.5° C.

Preparation of Resolving Agent 2
N-p-Chlorobenzenesulfonyl-L-phenylalanine (N-pClBs-L-Phe)

A mixture of L-phenylalanine 1.65 g (10 mmol) and 2N sodium hydroxide aqueous solution 5 ml was cooled in an ice-water bath. Under vigorous stirring a mixture of p-chlorobenzenesulfonyl chloride 2.32 g (11 mmol) and tetrahydrofuran 3 ml, and 2 N sodium hydroxide aqueous solution 6 ml was added dropwise and alternately each in three portions. After completion of the addition stirring was continued- under ice-water cooling for 5 minutes, and further, at room temperature for 1 hour. 6N hydrochloric acid 2 ml was added, and the sulfonamide was extracted with 80 ml of methyl isobutyl ketone. Organic layer was dried and the solvent distilled off to give a crude oil. 2.05 g of crystal-line N-pClBs-L-Phe was obtained by trituration of the oil with benzene.

Yield: 60.4%. Melting point: 132.0°–134.0° C.

The above described procedures were repeated for various N-Ars-L-Phe (in compound II, the amino acid is L-phenylalanine) in which Ar-groups are different, and all the crystals obtained from oily substances were once recrystallized. The yields and the melting points of the recrystallized products are shown in Table 1.

TABLE 1

| No. | Ar in N-Ars-L-Phe | Yield after Single Recrystallization (%) | Melting Point (°C.) |
|---|---|---|---|
| 1 | phenyl | 83.8 | 121.0–123.0 |
| 2 | 2-methylphenyl | 34.8 | 98.0–102.0 |
| 3 | 4-methylphenyl | 60.4 | 160.0–161.5 |
| 4 | 4-ethylphenyl | 88.3 | 130.0–132.0 |
| 5 | 4-t-butylphenyl | 66.8 | 111.0–113.0 |
| 6 | 2,5-dimethylphenyl | 68.5 | 125.0–128.0 |
| 7 | 2,4,6-trimethylphenyl | 79.0 | 71.0–81.0 |
| 8 | 2,4,6-triisopropylphenyl | 32.5 | 86.0–90.0 |
| 9 | 4-chlorophenyl | 60.4 | 132.0–134.0 |
| 10 | 4-bromophenyl | 43.8 | 139.0–141.0 |
| 11 | 4-methoxyphenyl | 84.2 | 141.0–143.0 |
| 12 | 2-nitrophenyl | 78.3 | 136.5–138.5 |
| 13 | 3-nitrophenyl | 36.6 | 160.0–161.5 |
| 14 | 4-nitrophenyl | 49.1 | 163.0–165.0 |
| 15 | 1-naphthyl | 54.6 | 136.0–138.0 |
| 16 | 2-naphthyl | 78.6 | 147.0–149.0 |

In Table 1, data No.9 are those already given in the above description.

Preparation of Resolving Agent 3
N-Tosyl-D-phenylglycine (N-Ts-D-PG)

To an ice-cooled mixture of D-phenylglycine 4.53 g (30 mmol), water 15 ml and 2N sodium hydroxide aqueous solution 36 ml, under vigorous stirring, a mixture of p-toluenesulfonyl chloride 6.86 g (36 mmol) and tetrahydrofuran 7 ml was added dropwise. Stirring was continued after completion of addition under ice-water cooling for 10 minutes, then, at room temperature for 1 hour. 2N hydrochloric acid 21.5 ml was added and resulting precipitate of crude N-Ts-D-PG was separated by filtration. The crude crystal was rinsed with water and dried. The product weighed 7.10 g. Yield: 77.6%. The crude crystal was once recrystallized from water-isopropanol mixture to give 5.85 g of fine crystal. The overall yield: 63.9%. Melting point: 172.0°–176.0° C.

Preparation of Resolving Agent 4
N-Methanesulfonyl-D-phenylalanine (N-Ms-L-Phe)

To a solution of L-phenylalanine 1.65 g (10 mmol) in 2N sodium hydroxide aqueous solution, cooled in an ice-water bath and under vigorous stirring, a mixture of methanesulfonyl chloride 1.26 g (11 mmol) and tetrahydrofuran 3 ml, and 2N sodium hydroxide aqueous solution 6 ml were added dropwise and alternately each in three portions. After completion of addition stirring was continued under ice-water cooling for 5 minutes, further, at room temperature for 1 hour. 6N hydrochloric acid 2 ml was added, and extraction was made with 30 ml of chloroform. Organic layer was washed with water and dried, and the solvent distilled off to obtain crude N-Ms-L-Phe as an oil. The crude product was purified by silica gel column chromatography- (eluent: chloroform, ethyl acetate) to give pure N-Ms-L-Phe 1.00 g as an oil. The yield based on the used L-phenylalanine was 41.0%.

Preparation of Resolving Agent 5
N-Tosyl-L-alanine (N-Ts-L-Ala)

L-Alanine 17.82 g (0.20 mol) was dissolved in 2N sodium hydroxide aqueous solution 100 ml. p-Toluenesulfonyl chloride 41.90 g (0.22 mol) was added to the resulting solution. Under vigorous stirring 2N sodium hydroxide aqueous solution was added dropwise to keep pH of the reaction mixture at around 9. After 2–3 hours the solution reached to a constant pH value. Unreacted acid chloride was removed by filtration and conc. hydrochloric acid was added to acidify the solution to pH 0.5 or lower. The resulting oily substance crystallized on cooling. 40.0G of white crystal was obtained after filtering, rinsing with water and drying. Yield: 82.3%

Melting point: 133.5°–134.5° C. (135°–6° C. by Sakota et al, Nihon Kagaku Kaishi, 90 (1) 77, (1969)) Purity (alkalimetric titration): 99.9%

Preparation of Resolving Agent 6

The above described procedures were repeated to prepare p-toluenesulfonamides from various L-amino acids. The yields and the melting points are shown in Table 2.

TABLE 2

| | | Resolving Agents | | |
|---|---|---|---|---|
| No. | L-Amino acid | Yield (%) | M.P. (°C.) Observed | M.P. (°C.) Literature* |
| 2 | valine | 92.6 | 149.5–150.5 | 148–9 |
| 3 | leucine | 95.2 | 123.5–125 | 123–4 |
| 4 | isoleucine | 89.7 | 134–136.5 | 130–2 |
| 5 | methionine | 96.7 | >120 | 179–80 |

*Sakota et al, Nihon Kagaku Kaishi, 90 (1) 77, (1969); McChesney et al, J. Am. Chem. Soc., 59 1116–8 (1937)

Preparation of Resolving Agent 7
N-Tosyl-L-Phenylalanine (N-Ts-L-Phe)

Water 320 kg and L-phenylalanine (L-Phe) 35.0 kg were charged in a 500 liters glass-lined reactor, and 30% sodium hydroxide solution 28 kg was added thereto. The mixture was heated to 35° C. to dissolve the charged L-Phe. 44 kg of p-toluenesulfonyl chloride (molar ratio 1.1 to L-Phe) was added in the form of powder, and 30% sodium hydroxide solution was added dropwise to keep pH of the reaction mixture at 9–10.5. The reaction was regarded as finished when the pH became constant. It took about 5 hours to attain the constant pH, and the final pH was 12–12.5.

35% hydrochloric acid 31.5 kg was added dropwise at 40°–45° C. to precipitate the tosylamide. Over about 3 hours pH was lowered to 1 or less and the temperature to 25° C. The precipitate was filtered by a centrifuge, and rinsed with water until pH of the rinsing water rose to 4 or higher.

The filter cake 110 kg (net weight 67 kg) was suspended in methanol 270 kg, and heated to 55° C. to dissolve the cake. Crystals appeared at 45°–48° C. by gradually cooling the solution and were centrifuged at room temperature, rinsed with 60% methanol 40 kg. After drying 57–58 kg of N-Ts-L-Phe (yield: 84–86%) was obtained. Melting point: 162°–165° C. Purity (titration): 99.5% Optical purity (HPLC): 99% or more.

EXAMPLE 1

(RS)-PBC 1.85 g (10 mmol) and N-Ts-L-Phe 3.19 g (10 mmol) were dissolved in methanol 28 ml under heating. To the solution 1 mg of previously prepared (S)-PBC•N-Ts-L-PHe salt was added as seed, and the solution stood still overnight. Separation of the precipitated crystal by filtration gave a diastereomer, (S)-PBC•N-Ts-L-Phe (crude salt), 2.49 g.

The crude salt was recrystallized from methanol to give purified (S)-PBC•N-Ts-L-Phe 2.39 g.

Melting point: 171.0°–173.0° C.

Specific Rotation: $[\alpha]_D^{23}+10.9°$ (C=0.974 MeOH)

Yield: 94.8% based on (S)-PBC in the racemate (half an amount of (RS)-PBC)

The repeated recrystallization of the above salt from methanol gave no change in melting point and the specific rotation. It is evident that single recrystallization is sufficient to purify the diastereomeric salt.

A chart of IR-spectrum of the purified (S)-PBC•N-Ts-L-Phe salt is shown in FIG. 1.

A portion, 0.50 g, of the above obtained purified salt was dissolved in methanol 3 ml together with triethylamine 0.18 g. To this mixture a solution of di-t-butyl dicarbonate 0.22 g in methanol 0.5 ml was added and the mixture was stirred at room temperature for 1 hour.

Solvent was distilled off from the reaction solution, and water 1 ml and 6N NaOH solution 0.2 ml were added to the residue, then, toluene 6 ml was added to extract (S)-(+)-N-t-butyl-4-t-butoxycarbonyl-2-piperazinecarboxamide (herein-after abbreviated as "(S)-Boc-PBC"). The toluene layer was dried and the solvent distilled off. (S)-Boc-PBC was obtained as an oil, which crystallized by treating with n-hexane 1 ml. Product: 0.26 g Specific Rotation: $[\alpha]_D^{21}+26.5°$ (C=1.008 MeOH)

Optical Purity: 100%(by HPLC using "Chiralpak AS", Daicel Chemical)

Melting point: 97.5°–100° C.

$^1$H-NMR (solvent CDCl$_3$, TMS as an internal standard)
 1.35 ppm (s, 9H);
 1.46 ppm (s, 9H);
 1.84 ppm (br, 1H);
 2.7–3.0 ppm (m, 4H);
 3.18–3.21 ppm (q, 1H);
 3.85 ppm (br, 1H);

4.06–4.08 ppm (br, 1H);

6.50 ppm (br, 1H)

Yield: 90% based on the pure salt; 85% based on the used (S)-PBC in (RS)-PBC

By adding 6N HCl 0.3 ml to acidify the water layer remaining after extraction of (S)-Boc-PBC, 0.31 g of N-Ts-L-Phe was recovered. Recovery: 98%

EXAMPLE 2

(RS)-PBC 1.85 g (10 mmol) and N-Ts-L-Phe 1.75 g (5.5 mmol) were heated to dissolve in methanol 19 ml. Previously prepared (S)-PBC•N-Ts-L-Phe salt 1 mg was added to the solution as seed, and the solution stood still overnight at room temperature. Precipitated diastereomeric salt was filtered off to obtain crude (S)-PBC•N-Ts-L-Phe 2.18 g.

The diastereomeric salt was recrystallized from methanol once to give 2.06 g of pure salt. The overall yield was 81.6%.

Melting point: 170.5°–172.5° C.

Treating 0.50 g of pure salt by the same procedures as in Example 1 gave 0.24 g of (S)-Boc-PBC. The yield based on the purified salt was 86%, and the overall yield based on (S)-PBC in the (RS)-PBC was 70%.

Melting point: 97.5°–100° C.

Specific Rotation: $[\alpha]_D^{23}$ +26.8° (C=1.014 MeOH)

Optical Purity: 100% (HPLC)

EXAMPLE 3

(RS)-PBC 0.37 g (2 mmol) and N-Ts-D-PG 0.61 g (2 mmol) were dissolved in 4.4 ml of a mixture of benzene:ethanol=10:1 under heating. 1 Mg of previously prepared (R)-PBC•N-Ts-D-PG salt was seeded in this solution, and the solution stood still overnight. The precipitated diastereomeric salt was separated by filtration, and (R)-PBC•N-Ts-D-PG crude salt 0.53 g was obtained.

Yield of the salt based on (R)-PBC in the used (RS)-PBC was 109%.

The above crude salt 0.53 g was treated by the method as in Example 1, and (R)-Boc-PBC 0.28 g was obtained. Yield based on the crude salt was 92%, and that based on (R)-PBC in the used (RS)-PBC was 100%.

Specific Rotation: $[\alpha]_D^{23}$ −15.8° (C=1.012 MeOH)

Optical Purity: 67% (HPLC)

EXAMPLE 4

(RS)-PBC 0.74 g (4.0 mmol) and N-Ts-L-Phe 1.02 g (3.2 mmol) were dissolved in a mixture of methanol 5.1 ml and water 0.9 ml under heating. 1 Mg of previously prepared (S)-PBC•N-Ts-L-Phe salt was seeded, and the solution stood still overnight. The precipitated diastereomeric salt was separated by filtration, and crude (S)-PBC•N-Ts-L-Phe salt 0.93 g was obtained. The yield of the salt based on (S)-PBC in the used (RS)-PBC was 92.2%, and optical purity of (S)-PBC in the salt was 98.0% e.e. (HPLC).

The above described experiments were repeated with different quantities of the resolving agent and proportions of water/methanol in the solvent. The results are shown in Table 3.

TABLE 3

| No. | N-Ts-L-Phe/ (RS)-PBC Molar Ratio | H₂O in Solvent (%) | Volume of Solvent (ml/g(RS)-PBC) | Yield of Crude Salt (%) | Optical Purity of (S)-PBC (% e.e.) |
| --- | --- | --- | --- | --- | --- |
| 1 | 0.6 | 15 | 8.1 | 77.8 | 98.7 |
| 2 | 0.6 | 30 | 8.1 | 71.6 | 98.8 |
| 3 | 0.55 | 50 | 8.1 | 76.6 | 94.2 |
| 4 | 0.7 | 0 | 8.1 | 96.0 | 98.8 |
| 5 | 0.7 | 15 | 8.1 | 86.2 | 96.7 |
| 6 | 0.7 | 30 | 8.1 | 82.6 | 97.3 |
| 7 | 0.7 | 50 | 8.1 | 89.0 | 97.4 |
| 8 | 0.8 | 10 | 8.1 | 91.0 | 98.1 |
| 9 | 0.8 | 15 | 8.1 | 92.2 | 98.0 |
| 10 | 0.8 | 16.7 | 8.1 | 87.0 | 96.8 |
| 11 | 0.8 | 30 | 8.1 | 86.0 | 99.0 |

In Table 3, the optical purities of (S)-PBC are those of crude salts. Data No.9 are those already mentioned in the description.

EXAMPLE 5

(RS)-PBC 0.37 g (2.0 mmol) and N-Ts-L-Phe 0.38 g (1.2 mmol) were dissolved in water 4.0 ml under heating. To the resulting solution, 1 mg of previously prepared of (S)-PBC•N-Ts-L-Phe salt was added and the solution stood still overnight. The precipitated crystal was separated by filtration, and crude (S)-PBC•N-Ts-L-Phe salt 0.40 g was obtained. The yield of the salt based on (S)-PBC in the used (RS)-PBC was 80.0%. Optical purity of (S)-PBC in the salt was 93.6% e.e.(HPLC).

EXAMPLE 6

(RS)-PBC 0.74 g (4.0 mmol) and N-Ts-L-Phe 0.89 g (2.8 mmol) were dissolved in 6 ml of 1-butanol under heating, and 1 mg of previously prepared (S)-PBC•N-Ts-L-Phe salt was added. The solution stood still overnight, and crude (S)-PBC•N-Ts-L-Phe salt 0.84 g was obtained. The yield of the salt based on (S)-PBC in the used (RS)-PBC was 83.8%. Optical purity of (S)-PBC in the salt was 97.7% e.e.(HPLC).

The above resolutions of Examples 5 and 6 were repeated with varied quantities of the resolving agent, and varied compositions and quantities of the solvents used. The results are shown in Table 4.

TABLE 4

| No. | N-Ts-L-Phe/ (RS)-PBC Molar Ratio | Composition of Solvent | Volume of Solvent (ml/g (RS)-PBC) | Yield of Crude Salt (%) | Optical Purity of (S)-PBC (% e.e.) |
| --- | --- | --- | --- | --- | --- |
| 1 | 0.7 | 15% H₂O/EtOH | 8.1 | 76.6 | 96.9 |
| 2 | 0.55 | 5% H₂O/n-PrOH | 10.8 | 76.4 | 99.4 |
| 3 | 0.7 | 30% H₂O/i-PrOH | 8.1 | 69.4 | 94.7 |
| 4 | 0.7 | 1-BuOH | 8.1 | 83.8 | 97.7 |
| 5 | 0.7 | 5% H₂O/1-BuOH | 8.1 | 63.8 | 98.6 |
| 6 | 0.7 | 10% H₂O/i-BuOH | 8.1 | 60.4 | 92.6 |
| 7 | 0.7 | 15% H₂O/i-BuOH | 8.1 | 39.0 | 99.2 |
| 8 | 0.7 | 5% H₂O/1-PenOH | 8.1 | 90.4 | 95.4 |
| 9 | 0.7 | 5% H₂O/1-HexOH | 8.1 | 88.2 | 95.7 |

In Table 4, data No.4 are those already-mentioned in the description. EtOH is an abbreviation of ethanol; PrOH, of propanol; BuOH, of butanol; PenOH, of pentanol; and HexOH, of hexanol, respectively.

EXAMPLE 7

(RS)-PBC 0.56 g (3.0 mmol) and N-pClBs-L-Phe 1.02 g (3.0 mmol) were dissolved in methanol 6 ml under heating, and 1 mg of previously prepared (S)-PBC•N-pClBs-L-Phe salt was seeded. The solution stood still at room temperature overnight, from which (S)-PBC•N-pClBs-L-Phe crude salt 0.75 g was obtained. The yield of the salt based on (S)-PBC in the used (RS)-PBC was 95.0%. Optical purity of (S)-PBC in the crude salt was 97.0%e.e.(HPLC).

EXAMPLE 8

The procedures the same as those of Example 7 were carried out using resolving agents, N-Ars-L-Phe (formula II, n=1), in which Ar group was varied, and methanol or ethanol as the solvent. The results are shown in Table 5.

TABLE 5

| No | Ar Group in N-Ts-L-Phe | Solvent | Volume of Solvent (ml/g(RS)-PBC) | Yield of Crude Salt (%) | Optical Purity of (R or S)-PBC (% e.e.) |
|---|---|---|---|---|---|
| 1 | phenyl | MeOH | 9.0 | 91.8 | 78.2(S) |
| 2 | 2-methylphenyl | MeOH | 18.0 | 99.8 | 97.3(S) |
| 3 | 4-ethylphenyl | MeOH | 10.8 | 97.0 | 93.2(S) |
| 4 | 4-t-butylphenyl | MeOH | 10.8 | 84.4 | 98.4(S) |
| 5 | 2,5-dimethylphenyl | MeOH | 9.0 | 101.8 | 84.2(S) |
| 6 | 2,4,6-trimethylphenyl | MeOH | 10.8 | 39.0 | 94.0(S) |
| 7 | 2,4,6-tri-i-propylphenyl | EtOH | 13.0 | 67.4 | 90.4(R) |
| 8 | 4-chlorophenyl | MeOH | 10.8 | 95.0 | 97.0(S) |
| 9 | 4-bromophenyl | MeOH | 21.6 | 95.8 | 97.2(S) |
| 10 | 4-methoxyphenyl | MeOH | 19.8 | 80.4 | 89.8(S) |
| 11 | 2-nitrophenyl | MeOH | 10.8 | 69.6 | 94.6(S) |
| 12 | 3-nitrophenyl | EtOH | 10.8 | 106.1 | 46.1(S) |
| 13 | 4-nitrophenyl | EtOH | 10.8 | 19.8 | 93.2(S) |
| 14 | 1-naphthyl | EtOH | 10.8 | 74.0 | 94.6(S) |
| 15 | 2-naphthyl | EtOH | 16.2 | 117.0 | 67.9(S) |

In Table 5, the optical purities of (R, S)-PBC are those in the crude salts.

EXAMPLE 9

(RS)-PBC 0.56 g (3.0 mmol) and N-Ts-D-PG 0.92 g (3.0 mmol) were dissolved in a mixture of benzene 6 ml and ethanol 0.6 ml under heating. After the addition of 1 mg of previously prepared (R)-PBC•N-Ts-D-PG salt, the solution stood still overnight, from which (R)-PBC•N-Ts-D-PG crude salt 1.11 g was obtained. The yield based on (R)-PBC in the used (RS)-PBC was 150.8%. The above crude salt was recrystallized from benzene-ethanol mixed solvent twice to give 0.60 g of purified (R)-PBC•N-Ts-D-PG salt. The yield based on (R)-PBC in the used (RS)-PBC was 82.0%. Optical purity of (R)-PBC in the purified (R)-PBC•N-Ts-D-PG salt was 97.7% e.e.(HPLC).

EXAMPLE 10

(RS)-PBC 0.74 g (4.0 mmol) and N-Ms-L-Phe 0.97 g (4.0 mmol) were dissolved in ethanol 7 ml under heating. To the resulting solution, 1 mg of previously prepared (S)-PBC•N-Ms-L-Phe salt was added. The solution stood still at room temperature overnight, from which (S)-PBC•N-Ms-L-Phe crude salt 0.40 g was obtained. The yield of the salt based on (S)-PBC in the used (RS)-PBC was 46.6%. Optical purity of (S)-PBC in the crude salt was 98.5% e.e.(HPLC).

EXAMPLE 11

(RS)-PBC 15.0 kg (81.0 gmol) and N-Ts-L-Phe 20.7 kg (64.8 gmol) were dissolved in 85% methanol 105 liters under heating. Under gradual cooling and stirring of the hot solution, 50 g of previously prepared (S)-PBC•N-Ts-L-Phe was added at 62° C., and the seeded solution was further cooled to 20° C. over about 5 hours. Precipitated crystal was separated by filtration and rinsed with a small amount of methanol. The (S)-PBC•N-Ts-L-Phe salt thus obtained was dried at 60° C. overnight. Product: 18.8 kg (37.2 gmol) The yield based on half the amount of (RS)-PBC used was 92%, and optical purity of (S)-PBC in the salt was 100% e.e. (HPLC).

The salt obtained above was then introduced into methanol 140 liters, and triethylamine 7.7 kg (76.1 gmol) was added thereto. A solution of di-t-b-utyl dicarbonate 8.1 kg (37.2 gmol) in methanol 15 kg was slowly added to the above solution to cause reaction. After distilling off about 100 liters of methanol, water 125 liters and toluene 60 kg were added to the concentrated solution. The toluene layer was separated, and the remaining water layer was subjected to extraction twice using toluene 60 kg each. Collected toluene layer was concentrated to about 18 kg. After addition of methylcyclohexane 40 kg, the mixture was heated to 50° C. for dissolution, cooled for separation of precipitated crystal by filtration. The filtered crystal was rinsed with methylcyclohexane 10 kg, and dried at 60° C. under vacuum. The obtained (S)-Boc-PBC weighed 8.5 kg (29.8 gmol), and the optical purity thereof was 100% e.e.(HPLC).

As the solvent for extracting the Boc-PBC, xylenes, chlorobenzenes, ethyl acetate, n-butanol and isobutanol may be used instead of the above used toluene. As to the solvent for crystallization, not only methylcyclohexane but also aliphatic and cycloaliphatic hydrocarbons such as hexane and cyclohexane can be used.

The mother liquor resulting from the first separation of (S)-PBC•N-Ts-L-Phe, about 120 liters, was concentrated by distilling off the methanol to about 30 liters. Water 100 liters was added to the concentrate and then conc. hydrochloric acid 11.5 kg to make the liquor strongly acidic. After the precipitated N-Ts-L-Phe was filtered off, the filtrate was just neutralized by addition of caustic soda, and concentrated to 35 liters. 8.7 Kg of 30% caustic soda solution was added to the liquor, and PBC was extracted therefrom with n-propanol 60 kg. The organic layer was concentrated to 28 kg, and 180 g of caustic soda flake was added. The mixture was refluxed for 1 hour, and the solvent distilled off to give crude PBC 8 kg. The optical purity determined by HPLC was 2% e.e., showing that racemization completed.

To extract PBC from the alkaline solution n-butanol and iso-butanol may be used in place of n-propanol.

The water layer, which was separated from the toluene layer after Boc-protection of (S)-PBC, was acidified with hydrochloric acid to recover N-Ts-L-Phe. The recovered N-Ts-L-Phe from the salt and the mother liquor weighed 19.2 kg in total, with recovery 93%. The dried acid has a melting point of 160°–161° C. and an optical purity of 100% e.e. It can be reused in the next resolution without purification.

EXAMPLE 12

(RS)-PBC 1.85 g (10 mmol) and N-Ts-L-Ala 2.43 g (10 mmol) were dissolved in ethanol 6 g under heating. 1 Mg of previously prepared (R)-PBC•N-Ts-L-Ala salt was added, and the solution stood still overnight at room temperature. The precipitated crystal was separated by filtration to obtain (R)-PBC•N-Ts-L-Ala (crude salt) 1.88 g. The yield based on (RS)-PBC was 43.9%, and the optical purity of (R)-PBC in the salt determined by HPLC was 90.4% e.e.

The salt 1.0 g was dissolved in ethanol 4 g heated at 60°–65° C. and the resulting solution was cooled. Filtration of the precipitated crystal gave the purified salt 0.7 g.

Melting point: 171.0°–172.0° C.

Optical purity of (R)-PBC in the salt was 99.97% (HPLC).

Rotation of the purified salt: $[\alpha]_D^{25}$+4.83° (C=2.0, MeOH).

Figure 2:
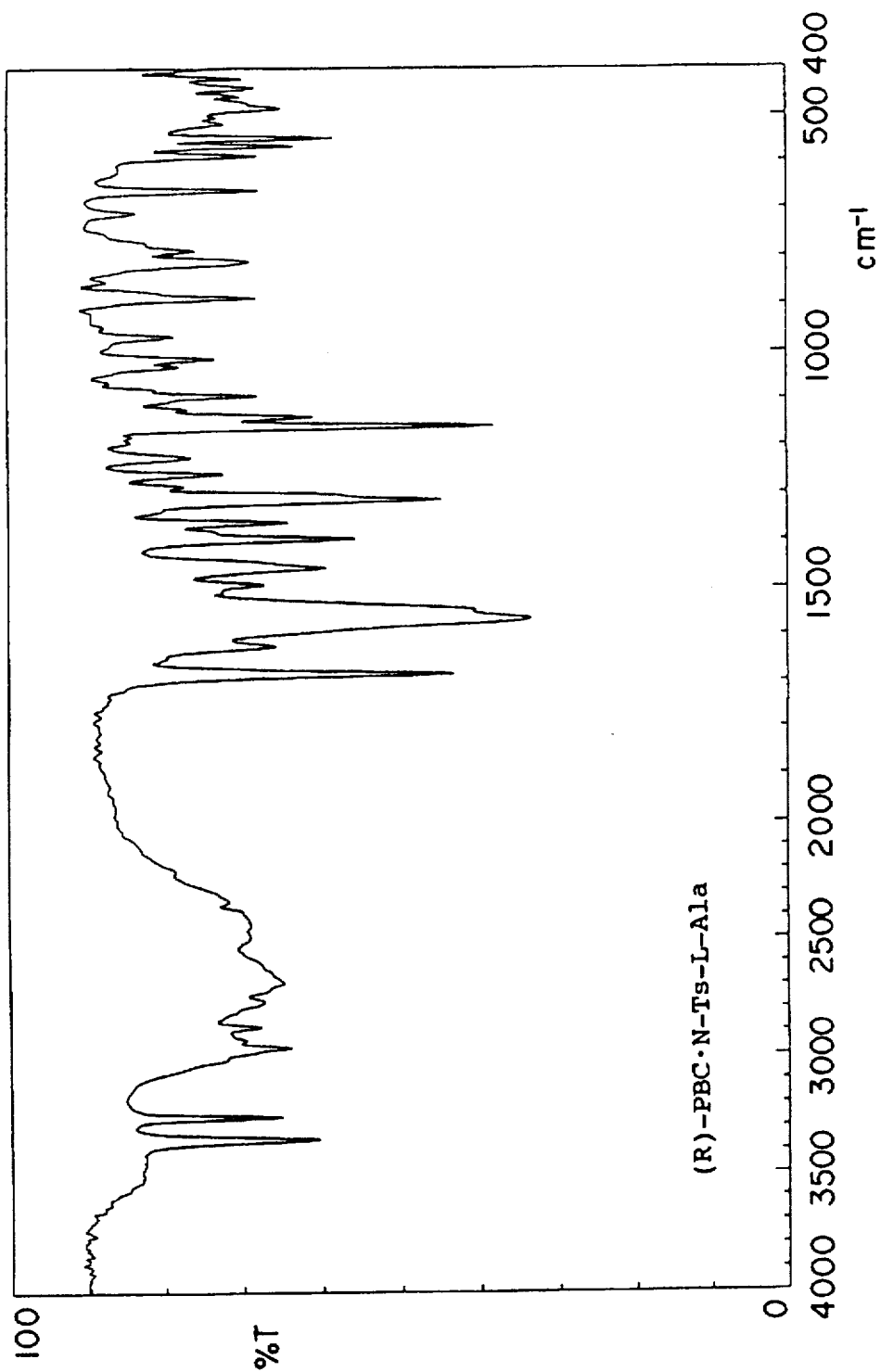
FIG. 2 is a chart of IR absorption spectrum of purified salt of (R)-N-t-butyl-2-piperazinecarboxamide N-tosyl-L-alanine, which is a diastereomeric salt obtained in working example 12.

IR-spectrum of the purified salt is shown in FIG. 2.

EXAMPLE 13

(RS)-PBC 1.85 g (10 mmol) and N-Ts-L-Val 2.71 g (10 mmol) were dissolved in ethanol 7 g under heating. 1 Mg of previously prepared (S)-PBC·N-Ts-L-Val salt was added, and the solution stood still overnight. Precipitated crystal was separated by filtration to obtain (S)-PBC·N-Ts-L-Val, 1.70 g. The yield based on (RS)-PBC was 37.3%, and the optical purity of (S)-PBC in the salt determined by HPLC was 84.3%.

The salt 1.0 g was dissolved in ethanol 2 g heated at 60°–65° C. and the resulting solution was cooled. Filtration of the precipitated crystal gave the purified salt 0.71 g.

Melting point: 180.0°–182.0° C.

Optical purity of (S)-PBC in the purified salt: 99.2%

Rotation of the purified salt: $[\alpha]_D^{25}$+21.6° (C=2.0, MeOH).

Figure 3:
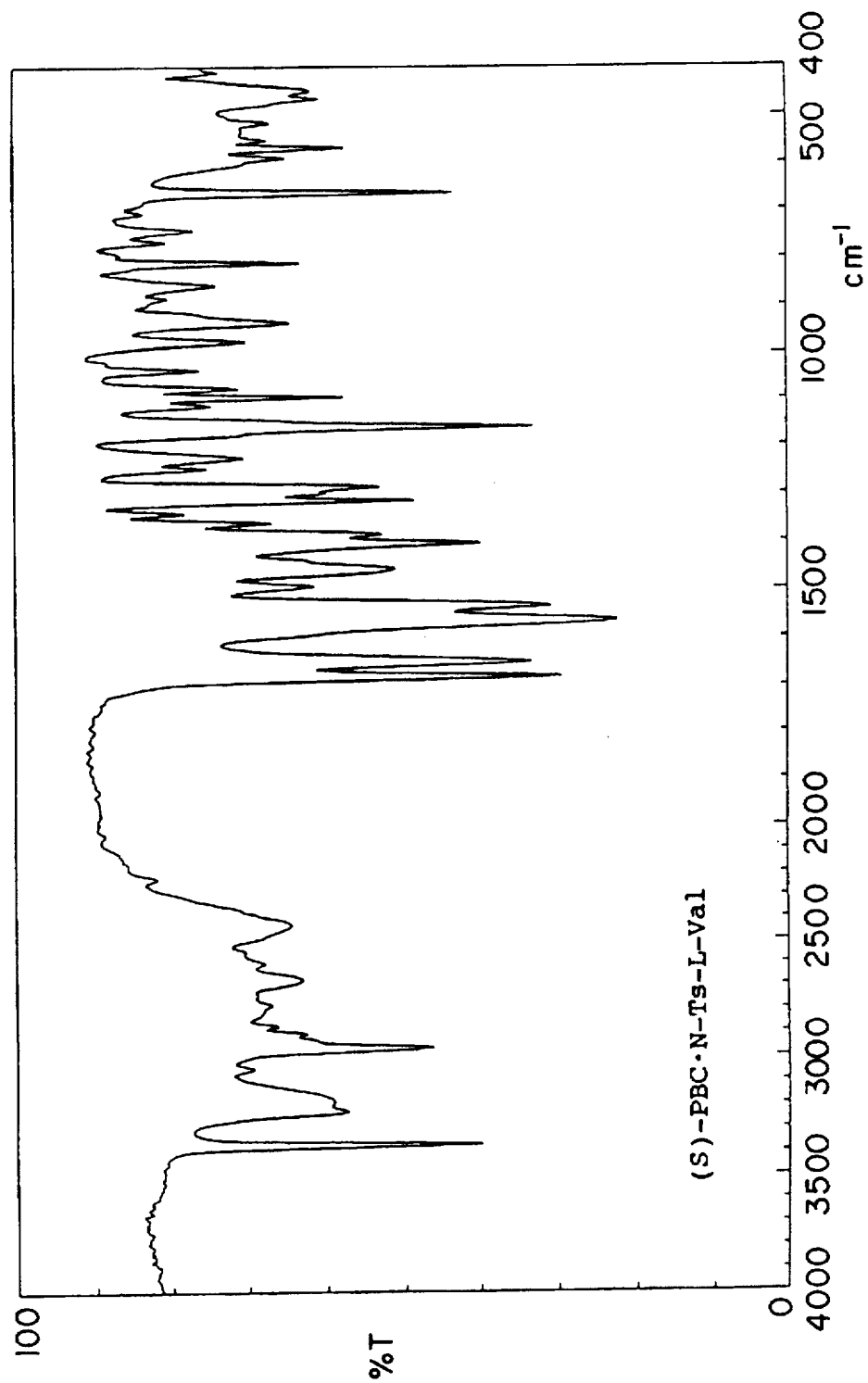
FIG. 3 is a chart of IR absorption spectrum of purified salt of (S)-N-t-butyl-2-piperazinecarboxamide N-tosyl-L-valine, which is a diastereomeric salt obtained in working example 13.

IR-spectrum of the purified salt is shown in FIG. 3.

EXAMPLES 14–16

1.85 Grams each of (RS)-PBC was resolved by the procedures as described in Example 13 using three kinds of resolving agents. The results are shown in Table. 6.

TABLE 6

| Examples | 14 | 15 | 16 |
|---|---|---|---|
| Resolving Agent | N-Ts-L-Leu | N-Ts-L-Ile | N-Ts-L-Met |
| Amount (g) | 2.85 | 2.85 | 3.03 |
| Diastereomeric Salt | | | |
| Weight (g) | 1.75 | 1.75 | 1.53 |
| Yield (%) | 37.2 | 37.2 | 31.3 |
| Optical Purity (% e.e.) | 60.6 | 79.5 | 96.3 |
| Purified Salt | | | |
| Optical Purity (% e.e.) | 95.9 | 96.8 | 100.0 |
| Melting Point (°C.) | 179.5–181.5 | 177–180.5 | 154.5–156 |

EXAMPLES 17–19

1.85 Grams each of (RS)-PBC (10 mmol) and 2.71 g each of N-Ts-L-Val were dissolved in the solvents shown in Table 7 under heating, and resolutions carried out by the procedures as in Example 13. Table 7 also shows the experimental results.

TABLE 7

| Examples | 17 | 18 | 19 |
|---|---|---|---|
| Solvent | methanol | n-butanol | water |
| Amount (g) | 5.3 | 161 | 6.8 |
| Diastereomeric Salt | | | |
| Yield/(RS)-PBC (%) | 8.8 | 24.4 | 18.0 |
| Optical Purity (% e.e.) | 60.3 | 95.8 | 40.8 |

EXAMPLES 20–22

The specific amounts of (RS)-PBC and N-Ts-L-Ala were dissolved in the solvents shown in Table 8, and resolutions carried out by the procedures of Example 13.

TABLE 8

| Examples | 20 | 21 | 22 |
|---|---|---|---|
| Solvent | water | methanol | 90%-isopropanol* |
| Amount (g) | 15.0 | 5.3 | 19.0 |
| (RS)-PBC (g) | 3.70 | 1.85 | 3.70 |
| N-Ts-L-Ala (g) | 4.86 | 2.43 | 3.89 |
| Molar Ratio | 1.0 | 1.0 | 0.8 |
| PBC Salt | | | |
| Yield/(RS)-PBC (%) | 29.8 | 26.8 | 28.0 |
| Optical Purity (% e.e.) | 90.4(S) | 89.1(R) | 97.7(R) |

*containing 10% water

The results in Table 8 show the steric configuration of PBC in the diastereomeric salts with N-Ts-L-Ala changes depending on the solvent used: S-enantiomer from water, and R-isomers from alcoholic solvents.

EXAMPLE 23

4.56 G of the purified (S)-PBC·N-Ts-L-Val prepared by the method of Example 13 was dissolved in methanol 30 ml together with triethylamine 2.03 g. Solution of di-t-butyl dicarbonate 2.18 g in methanol 5 ml was added to the resulting mixture, which was then stirred at room temperature for 1 hour. The solvent was distilled off, and, water 10 ml and 6N NaOH solution 2 ml were added to the residue. 60 Ml of toluene was used to extract (S)-Boc-PBC. The organic layer was dried with magnesium sulfate and the solvent distilled off. (S)-Boc-PBC was obtained as an oil, which crystallized by treatment with 10 ml of n-hexane. Product: 2.42 g Melting point: 97.5°–100° C. Optical purity was determined by HPLC using "Chiralpak AS" (Daicel Chemical) to be 100% e.e. Melting point of the purified product obtained by recrystallization from hexane is 107.5°–108.5° C.

We claim:

1. A process for preparing an optically active N-t-butyl-2-piperazinecarboxamide which comprises:

reacting in a reaction medium (RS)-N-t-butyl-2-piperazinecarboxamide of the formula:

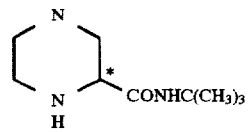

wherein * designates an asymmetric carbon atom, with a sulfonamide derivative of an optically active amino acid of the formula:

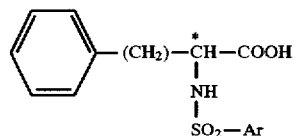

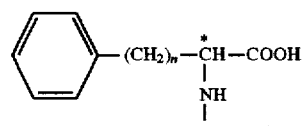

-continued or

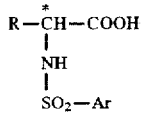

wherein * designates an asymmetric carbon; n=0 or 1; Alk is a $C_1$-$C_6$ alkyl group; R is a straight chain or branched chain $C_1$-$C_6$ alkyl group, a methylthioethyl group or a $C_1$-$C_2$ hydroxyalkyl group; and Ar is a phenyl or naphthyl group optionally substituted with one to three $C_1$-$C_6$ alkyl, halogen, nitro or $C_1$-$C_2$ alkoxy groups; to form diastereomeric salts of the formula:

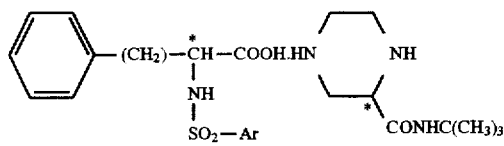

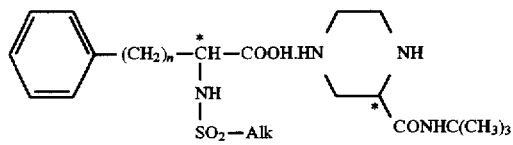

or

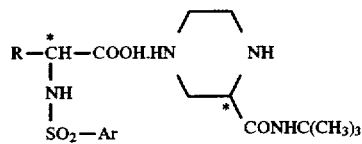

precipitating the less soluble diastereomeric salt from the medium;

separating the precipitated diastereomeric salt from the medium; and decomposing the diastereomeric salt which was separated from the medium to obtain optically active N-t-butyl-2-piperazinecarboxamide.

2. The process of claim 1, wherein the molar ratio of the sulfonamide derivative of the optically active amino acid to the (RS)-N-t-butyl-2-piperazinecarboxamide is from 0.1 to 2.0.

3. The process claim of claim 2, wherein the molar ratio is 0.5 to 1.0.

4. The process of claim 1, wherein the solvent is water, a lower alcohol, or a mixture of water and lower alcohol.

5. A process for preparing an optically active N-t-butyl-2-piperazinecarboxamide which comprises:

reacting in a reaction medium (R,S)-N-t-butyl-2-piperazinecarboxamide of the formula:

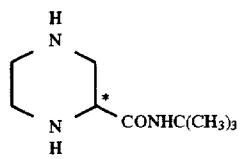

wherein * designates an asymmetric carbon atom, with a sulfonamide derivative of an optically active amino acid of the formula:

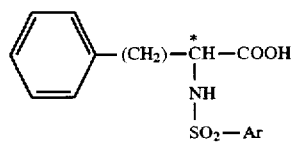

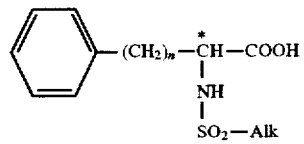

or

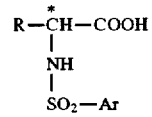

wherein * designates an asymmetric carbon; n=0 or 1; Alk is a $C_1$-$C_6$ alkyl group; R is a straight chain or branched chain $C_1$-$C_6$ alkyl group, a methylthioethyl group or a $C_1$-$C_2$ hydroxyalkyl group; and Ar is a phenyl or naphthyl group optionally substituted with one to three $C_1$-$C_6$ alkyl, halogen, nitro or $C_1$-$C_2$ alkoxy groups to form diastereomeric salts of the formula:

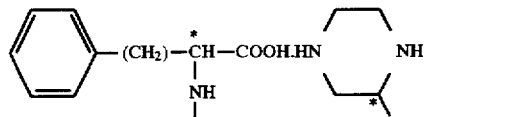

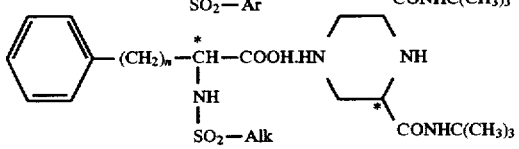

precipitating the less soluble diastereomeric salt from the medium;

separating the precipitated diastereomeric salt from the medium;

reacting the separated less soluble diastereomeric salt with a BOC-protecting agent in the presence of triethylamine to form a 4-t-butoxycarbonyl-N-t-butyl-2-piperazinecarboxamide; and recovering the BOC-protected optically active N-t-butyl-2-piperazinecarboxamide.

6. The process of claim 5, wherein the BOC-protecting agent is di-t-butyl dicarbonate.

7. A diastereomeric salt of the formula:

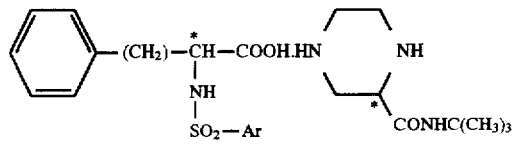

-continued

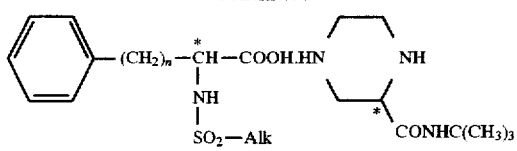

or

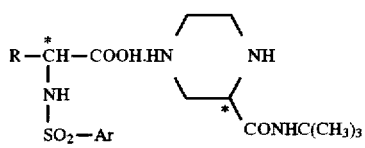

wherein * designates an asymmetric carbon atom; n=0 or 1; Alk is a $C_1$–$C_6$ alkyl group; R is a straight chain or branched chain $C_1$–$C_6$ alkyl group, a methylthioethyl group or a $C_1$–$C_2$ hydroxyalkyl group; and Ar is a phenyl or a naphthyl group optionally substituted with one to three $C_1$–$C_6$ alkyl, halogen, nitro or $C_1$–$C_2$ alkoxy groups.

8. The (S,S)-diastereomeric salt of claim 7 of the formula:

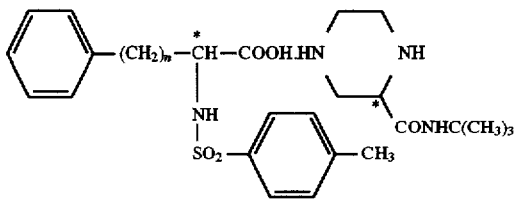

9. The (S,R)-diastereomeric salt of claim 7 of the formula:

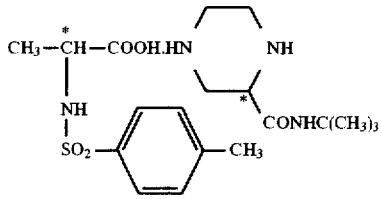

10. The (R,S)-diastereomeric salt of claim 7 of the formula:

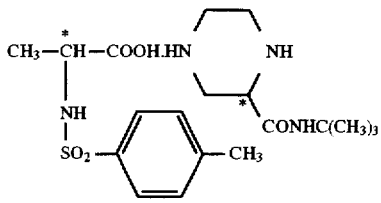

11. The (S,S)-diastereomeric salt of claim 7 of the formula:

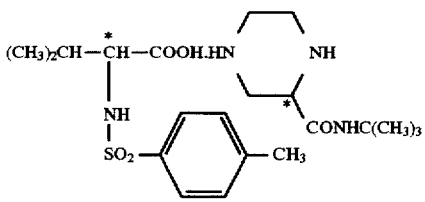

* * * * *